(12) United States Patent
Meadows et al.

(10) Patent No.: US 10,631,779 B2
(45) Date of Patent: Apr. 28, 2020

(54) METHOD FOR ADJUSTING A SYSTEM FOR STIMULATING A HYPOGLOSSAL NERVE

(71) Applicant: ImThera Medical, Inc., San Diego, CA (US)

(72) Inventors: Paul M. Meadows, Glendale, CA (US); Marcelo G. Lima, San Diego, CA (US); Faisal N. Zaidi, San Diego, CA (US); Jasper Benke, San Diego, CA (US)

(73) Assignee: ImThera Medical, Inc., Houston, TX (US)

( * ) Notice: Subject to any disclaimer, the term of this patent is extended or adjusted under 35 U.S.C. 154(b) by 66 days.

(21) Appl. No.: 15/492,079

(22) Filed: Apr. 20, 2017

(65) Prior Publication Data

US 2017/0215791 A1 Aug. 3, 2017

Related U.S. Application Data

(63) Continuation of application No. 14/898,956, filed as application No. PCT/US2015/041101 on Jul. 20, 2015, now Pat. No. 9,656,083.

(Continued)

(51) Int. Cl.
*A61N 1/36* (2006.01)
*A61B 5/00* (2006.01)

(Continued)

(52) U.S. Cl.
CPC ........ *A61B 5/4836* (2013.01); *A61B 5/02108* (2013.01); *A61B 5/0476* (2013.01);

(Continued)

(58) Field of Classification Search
CPC ................ A61N 1/3611; A61N 1/3605; A61N 1/36139; A61B 5/04; A61B 5/4047; A61B 5/4052; A61B 5/4818
See application file for complete search history.

(56) References Cited

U.S. PATENT DOCUMENTS 8,428,725 B2 4/2013 Meadows et al.
8,886,322 B2 11/2014 Meadows et al.
(Continued)

FOREIGN PATENT DOCUMENTS

WO 2016/014391 A1 1/2016

OTHER PUBLICATIONS

Search Report dated Jan. 4, 2018 for European Patent Application No. 15825256.9, 5 pp.

(Continued)

*Primary Examiner* — Tammie K Marlen
(74) *Attorney, Agent, or Firm* — Foley & Lardner LLP

(57) ABSTRACT

A method for titrating a stimulation parameter for one or more electrode contacts in a system for stimulating a hypoglossal nerve of a patient includes activating one of the one or more electrode contacts to stimulate the hypoglossal nerve of the patient, obtaining a first and/or second physiological measurement from the patient, comparing the first and/or second physiological measurement to a first and/or second predetermined target value, adjusting a stimulation parameter for the one of the one or more electrode contacts if the first and/or second physiological measurement differs from the first and/or second predetermined target value.

23 Claims, 2 Drawing Sheets

Related U.S. Application Data

(60) Provisional application No. 62/027,363, filed on Jul. 22, 2014.

(51) Int. Cl.

| | | |
|---|---|---|
| *A61N 1/05* | (2006.01) | |
| *A61B 5/087* | (2006.01) | |
| *A61B 5/145* | (2006.01) | |
| *A61B 5/021* | (2006.01) | |
| *A61B 5/0476* | (2006.01) | |
| *A61B 5/0488* | (2006.01) | |
| *A61B 5/0496* | (2006.01) | |
| *A61B 5/024* | (2006.01) | |
| *A61B 5/026* | (2006.01) | |
| *A61B 5/04* | (2006.01) | |

(52) U.S. Cl.
CPC .......... *A61B 5/0488* (2013.01); *A61B 5/0496* (2013.01); *A61B 5/087* (2013.01); *A61B 5/14542* (2013.01); *A61B 5/4818* (2013.01); *A61N 1/0556* (2013.01); *A61N 1/36* (2013.01); *A61N 1/3601* (2013.01); *A61N 1/3611* (2013.01); *A61N 1/36139* (2013.01); *A61N 1/36185* (2013.01); *A61B 5/021* (2013.01); *A61B 5/026* (2013.01); *A61B 5/02405* (2013.01); *A61B 5/04* (2013.01); *A61B 5/4047* (2013.01)

(56) References Cited

U.S. PATENT DOCUMENTS

| | | |
|---|---|---|
| 2005/0075680 A1 | 4/2005 | Lowry et al. |
| 2005/0137645 A1 | 6/2005 | Voipio et al. |
| 2011/0112601 A1 | 5/2011 | Meadows et al. |
| 2011/0202119 A1 | 8/2011 | Ni et al. |
| 2011/0264164 A1 | 10/2011 | Christopherson |
| 2012/0089199 A1 | 4/2012 | Bolea et al. |
| 2013/0253627 A1 | 9/2013 | Meadows et al. |
| 2014/0100642 A1 | 4/2014 | Mashiach |
| 2015/0148860 A1 | 5/2015 | Lima et al. |
| 2015/0224307 A1 | 8/2015 | Bolea |
| 2016/0199651 A1 | 7/2016 | Meadows et al. |

OTHER PUBLICATIONS

Hung, J. et al.: "Dilation of the oropharynx via selective stimulation of the hypoglossal nerve", Journal of Neural Engineering, vol. 2, No. 4, Aug. 2005, pp. 73-80.

Office Action dated Jan. 27, 2016 for Canadian Patent Application No. 2,641,821.

International Search Report and Written Opinion dated Oct. 23, 2015 for International Patent Application No. PCT/US15/41101.

Examination Report No. 1 dated Aug. 31, 2017 for Australian Patent Application No. 2015294336, 4 pp.

METHOD FOR ADJUSTING A SYSTEM FOR STIMULATING A HYPOGLOSSAL NERVE

CROSS-REFERENCE TO RELATED APPLICATIONS

This application is a continuation of U.S. patent application Ser. No. 14/898,956, filed Jul. 20, 2015, which is a U.S. National Stage of International Application No. PCT/US2015/041101, filed Jul. 20, 2015, which claims the benefit of U.S. Provisional Patent Application No. 62/027,363 filed Jul. 22, 2014, each of which is incorporated by reference herein in its entirety.

FIELD OF THE INVENTION

The present invention generally relates to methods for adjusting a system for stimulating a hypoglossal nerve of a patient. In some embodiments, the present invention relates to methods for adjusting or titrating one or more parameters for a system for stimulating the Hypoglossal nerve of a patient to prevent obstructive sleep apnea.

BACKGROUND OF THE INVENTION

Sleep apnea is a sleep disorder characterized by pauses in breathing during sleep. Those affected by sleep apnea stop breathing during sleep numerous times during the night. Obstructive sleep apnea (OSA) is caused by episodes of physical obstruction of the upper airway channel (UAW) during sleep. The physical obstruction is often caused by changes in the position of the tongue during sleep that results in the closure of the soft tissues lining the airway at the rear of the throat or pharynx.

OSA is characterized by the obstruction of the airway causing breathing to cease completely (Apnea) or partially (Hypopnea). The human airway at the level of the oropharynx is lined by soft tissue; any collapse of its walls results in the closure of the airway, which leads to insufficient air intake, thereby interrupting one's sleep (episodes or microarousals).

During sleep, the tongue muscles relax. In this relaxed state, the tongue may lack sufficient muscle tone necessary for maintaining the tongue's normal tonic shape and position. When the base of the tongue along with soft tissue of the upper airway collapses, the upper airway channel is blocked, causing an apnea event. Blockage of the upper airway prevents air from flowing into the lungs, creating a decrease in blood oxygen level and an increase in blood carbon dioxide level. The reduction in oxygen and increased carbon dioxide alert the brain to resume breathing. This causes a reflexive forced opening of the upper airway channel until normal patency is regained, followed by normal respiration until the next apneic event. These reflexive forced openings briefly arouse the patient from sleep.

OSA is a potentially life-threatening disease that often goes undiagnosed in most patients affected by sleep apnea. The severity of sleep apnea can be measured by dividing the number of episodes of apneas and hypopneas lasting ten seconds or more by the number of hours of sleep. The resulting number is called the Apnea-Hypopnea Index, or AHI. The higher the index the more serious the condition. An index between 5 and 10 is low, between 10 and 15 is mild to moderate, over 15 is moderately severe, and anything over 30 indicates severe sleep apnea.

Treatment options for OSA have not been consistently effective for all patients. A standard method for treating OSA is Continuous Positive Airway Pressure (CPAP) treatment, which requires the patient to wear a mask through which air is blown into the nostrils and mouth to keep the airway open. Patient compliance is poor due to discomfort and side effects such as sneezing, nasal discharge, dryness, skin irritation, claustrophobia, and panic attacks. Other treatments include invasive surgical procedures where rigid inserts are implanted in the soft palate to provide structural support or more drastic options such as uvulopalatopharyngoplasty, mandibular advancement, and tracheostomy.

Nerve stimulation to control the position of the tongue is a promising alternative to these forms of treatment. For example, pharyngeal dilation via Hypoglossal nerve stimulation has been shown to be an effective treatment method for OSA. The nerves are stimulated using an implanted electrode to displace the tongue and open the airway during sleep or to prevent the collapse of the tongue by improving or maintaining muscle tone and thereby maintain the patency of the airway. In particular, electrical stimulation of the medial hypoglossal nerve branch (i.e., innervating mainly the Genioglossus or protrusor muscles), has demonstrated significant reductions in UAW airflow resistance while electrical stimulation of the lateral branch (i.e., innervating Styloglossus and Hyoglossus or retrusor muscles) has demonstrated maintenance of tongue muscle tone. The latter may involve the targeted co-stimulation of both protrusor and retrusor muscles. The protrusor muscles may be stimulated at higher activation levels while retrusor muscles maybe stimulated at lower levels. In this manner, the forces generated by the activation of retrusor muscles is insufficient to displace the tongue backward or occlude the retroglossal airway, however at the same time, is enough to generate tongue tone or stiffness sufficient for maintaining the patency of the airway. In other words, the retrusive effect of the retrusor muscles at the rear of the tongue is rendered insignificant in the presence of protrusive forces in the front. Therefore the controlled co-activation of a different but small fraction of the retrusor (antagonist) musculature together with the activation of protrusor (agonist) muscles will improve oropharyngeal patency while not significantly leading to tongue retrusion. These two muscle groups, when contracting simultaneously, control both the tongue's position and its tone and stiffness.

While electrical stimulation of nerves has been experimentally shown to remove or ameliorate certain conditions (e.g., obstructions in the UAW), current implementation methods typically require accurate detection of a condition (e.g., a muscular obstruction of the airway or chest wall expansion), surgically selective stimulation of a muscle or nerve, and a coupling of the detection and stimulation. These systems rely on detection of breathing and/or detection of apnea events as pre-conditions to control and deliver electrical stimulation in order to cause only useful tongue motions and to periodically rest the tongue muscles and avoid fatigue. In one system, for example, a voltage controlled waveform source is multiplexed to two cuff electrode contacts. A bio-signal amplifier connected to the contacts controls stimulus based on breathing patterns. In another system, a microstimulator uses an implanted single-contact constant current stimulator synchronized to breathing to maintain an open airway. A third system uses an implantable pulse generator (IPG) with a single cuff electrode attached to the distal portion of the Hypoglossal nerve, with stimulation timed to breathing. This last system uses a lead attached to the chest wall to sense breathing motions by looking at "bio-impedance" of the chest wall. Still another system monitors vagus nerve electroneurograms to detect an apnea event and stimulate the Hypoglossal nerve in response.

One drawback of utilizing nerve stimulation to control the position of the tongue is that the muscle fibers activated by the stimulated nerve fibers will eventually fatigue if the applied stimulus is maintained at a sufficiently high enough frequency. If the muscle fibers become fatigued, muscle force and/or position then changes towards the relaxed, inactivated condition. Fatigue may be minimized or prevented by using a stimulation duty cycle—that is, stimulating for a certain amount of time before significant fatigue sets in, then stopping to let the muscle rest and regain its ability to contract. For obstructive sleep apnea, however, this method is less than optimal. Without an applied stimulus during the off period of the electrical stimulation duty cycle, the tongue would not be driven to maintain a desired position and could fall back against the rear of the throat and allow an apnea event to occur. This is one of the reasons that many OSA stimulation systems rely on sensors to detect when to apply stimulation and when to leave it off.

BRIEF SUMMARY OF THE INVENTION

In one embodiment there is a method for titrating a stimulation parameter for one or more electrode contacts in a system for stimulating a hypoglossal nerve of a patient, the method comprising: activating one of the one or more electrode contacts to stimulate the hypoglossal nerve of the patient; obtaining a first physiological measurement from the patient; comparing the first physiological measurement to a first predetermined target value; and adjusting a stimulation parameter for the one of the one or more electrode contacts if the first physiological measurement differs from the first predetermined target value. In a further embodiment, the method includes repeating the method until the first physiological measurement reaches the first predetermined target value or until the stimulation parameter reaches a pre-set limit.

In one embodiment, the stimulation parameter is changed incrementally during the adjustment steps. In one embodiment, the stimulation parameter is changed by a percentage of the existing value during each of the adjustment steps. In a further embodiment, the method includes wirelessly transmitting information to a display and/or recording device regarding which of the one or more electrode contacts is activated. In one embodiment, the information includes an identity of an activated electrode contact, and the method further comprising: generating a number of pulses corresponding to the identity of the activated electrode contact. In one embodiment, the information includes the amplitude of the activated electrode contact, and the method further comprising: a number of pulses corresponding to the amplitude range of the electrode contact and a constant level corresponding to the amplitude of the electrode contact within that range. In a further embodiment, the method includes obtaining a second physiological measurement from the patient, comparing the second physiological measurement to a second predetermined target value, and adjusting a stimulation parameter for the one of the one or more electrode contacts if the second physiological measurement differs from the second predetermined target value.

In one embodiment, the first and second physiological measurements are selected from the group consisting of nasal airflow, oral airflow, tidal volume, blood oxygen saturation level, blood pressure, peripheral arterial tone, pulse transit time, electroencephalography, electromyography, electrooculography, and combinations and/or derivatives thereof. In a further embodiment, the method is performed while the patient is asleep. In one embodiment, the adjustment of the stimulation parameter is paused while an arousal of the patient is detected, a worsening or altered condition of the first physiological measurement is detected, or a predetermined condition of the patient is detected.

In one embodiment, the system is configured for preventing obstructive sleep apnea in the patient. In one embodiment, the first predetermined target value is a value of a person who does not have obstructive sleep apnea. In one embodiment, the stimulation parameter is selected from the group consisting of stimulation amplitude, stimulation phase duration, stimulation frequency, contact group assignment, group or contact enablement, group ramp up time, group on time, group ramp down time, group gap time, group population percentage, inter- and intra-therapeutic periodicity, and combinations thereof. In one embodiment, the first physiological measurement is selected from the group consisting of nasal airflow, oral airflow, tidal volume, blood oxygen saturation level, blood pressure, peripheral arterial tone, pulse transit time, electroencephalography, electromyography, electrooculography, and combinations and/or derivatives thereof. In a further embodiment, the method includes repeating the method for each of the one or more electrode contacts or groups in the system.

In one embodiment, wherein the one or more electrode contacts include a plurality of electrode contacts, each electrode contact being connected to an independent current source. In one embodiment, the system for stimulating a hypoglossal nerve of a patient includes six electrode contacts arranged on a cuff electrode and is configured for controlling a position of the patient's tongue.

In another embodiment, there is a method for titrating a stimulation parameter for one or more electrode contacts in a system for stimulating a hypoglossal nerve of a patient, the method comprising: activating one of the one or more electrode contacts to stimulate the hypoglossal nerve of the patient; obtaining a first physiological measurement from the patient; obtaining a second physiological measurement from the patient; comparing the first physiological measurement to a first predetermined target value; comparing the second physiological measurement to a second predetermined target value; adjusting a stimulation parameter for the one of the one or more electrode contacts if the first physiological measurement differs from the first predetermined target value or the second physiological measurement differs from the second predetermined target value; and repeating the method until the first physiological measurement reaches the first predetermined target value and/or the second physiological measurement reaches the second predetermined target value, or until the stimulation parameter reaches a pre-set limit.

In one embodiment, the first and second physiological measurements are selected from the group consisting of nasal airflow, oral airflow, tidal volume, blood oxygen saturation level, blood pressure, peripheral arterial tone, pulse transit time, electroencephalography, electromyography, electrooculography, and combinations and/or derivatives thereof. In one embodiment, the stimulation parameter is selected from the group consisting of stimulation amplitude, stimulation phase duration, stimulation frequency, contact group assignment, group or contact enablement, group ramp up time, group on time, group ramp down time, group gap time, group population percentage, inter- and intra-therapeutic periodicity, and combinations thereof. In a further embodiment, the method includes repeating the method for each of the one or more electrode contacts or groups in the system. In one embodiment, the system for stimulating a hypoglossal nerve of a patient includes six electrode contacts arranged on a cuff electrode and is configured for controlling a position of the patient's tongue.

In another embodiment, there is a method for titrating a stimulation parameter for one or more electrode contacts or groups in a system for stimulating a hypoglossal nerve of a patient, the method comprising: activating one of the one or more electrode contacts or groups to stimulate the hypoglossal nerve of the patient; obtaining a first physiological measurement from the patient when the one of the one or more electrode contacts or groups is activated; deactivating the one of the one or more electrode contacts or groups; obtaining a second physiological measurement from the patient when the one of the one or more electrode contacts or groups is deactivated; comparing the first and second physiological measurements to one another to determine a difference between the first and second physiological measurements; and adjusting a stimulation parameter for the one of the one or more electrode contacts or groups in response to the difference between the first and second physiological measurements.

In one embodiment, the first and second physiological measurements are airflow or tidal volume or derivative thereof measurements. In one embodiment, the first and second physiological measurements are blood oxygen saturation levels. In one embodiment, the stimulation parameter is selected from the group consisting of stimulation amplitude, stimulation phase duration, stimulation frequency, contact group assignment, group or contact enablement, group ramp up time, group on time, group ramp down time, group gap time, group population percentage, inter- and intra-therapeutic periodicity, and combinations thereof. In a further embodiment, the method includes repeating the method for each of the one or more electrode contacts or groups in the system.

BRIEF DESCRIPTION OF THE SEVERAL VIEWS OF THE DRAWINGS

The following detailed description will be better understood when read in conjunction with the appended drawings of an exemplary embodiment. It should be understood, however, that the invention is not limited to the precise arrangements and instrumentalities shown.

In the drawings.

DETAILED DESCRIPTION OF THE INVENTION

One method of minimizing or preventing muscle fatigue is to use one or more independent current sources to activate multiple portions of the desired muscle groups. This can be accomplished, for example, using OSA systems and methods such as those described in particular embodiments of U.S. Pat. No. 8,428,725, U.S. Patent Application Publication No. 2011/0112601, and U.S. Pat. No. 8,886,322, which are all incorporated herein by reference in their entirety. These systems and methods include attaching at least one electrode to the patient's Hypoglossal nerve and applying an electric signal through the electrode to a portion of the Hypoglossal nerve (e.g., at least one targeted motor efferent located within the Hypoglossal nerve) to stimulate at least one muscle of the tongue so as to control the position of the patient's tongue. The systems and methods may also include the use of more than one contact (e.g., six contacts or more) to target more than one motor efferent and allow for stimulation of more than one muscle. In some embodiments, the stimulation load to maintain the position of the tongue may be shared by each muscle.

Figure 1:
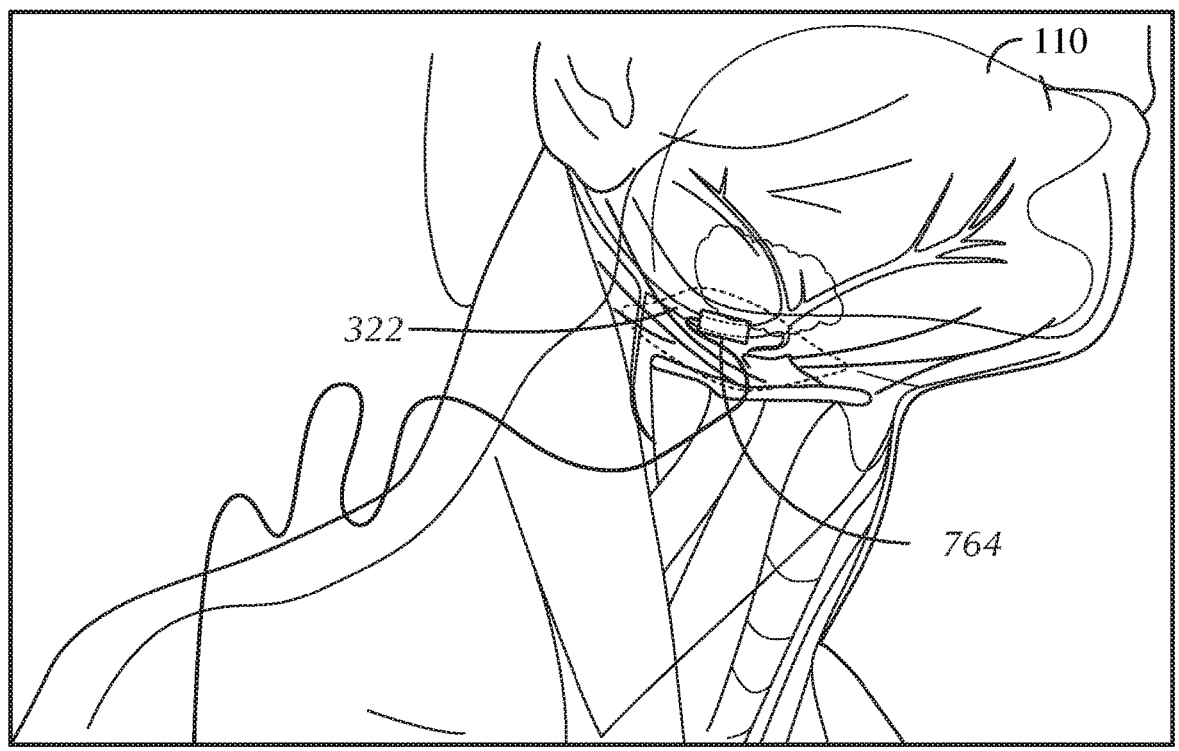
FIG. 1 is an exemplary illustration of an electrode attached to a patient's Hypoglossal nerve.
Figure 2:
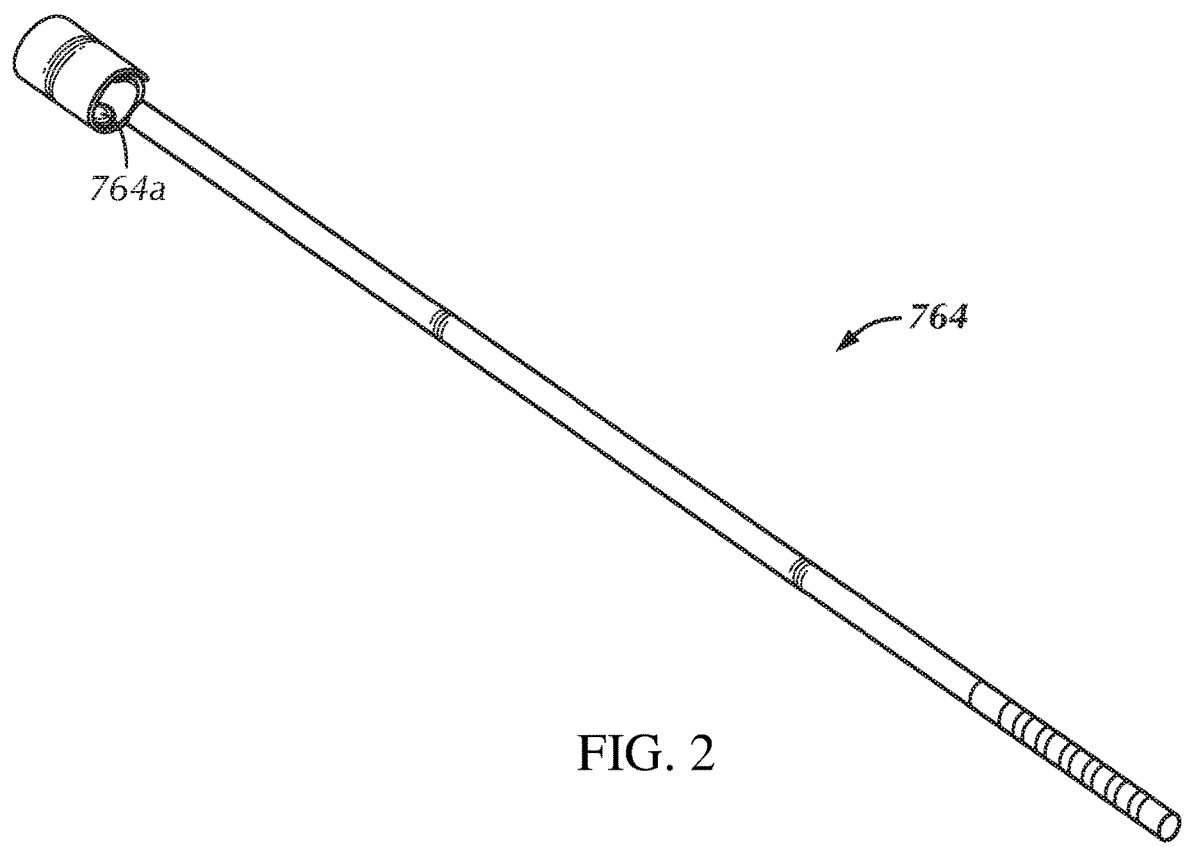
FIG. 2 is a perspective view of the electrode shown in FIG. 1.
Figure 3:
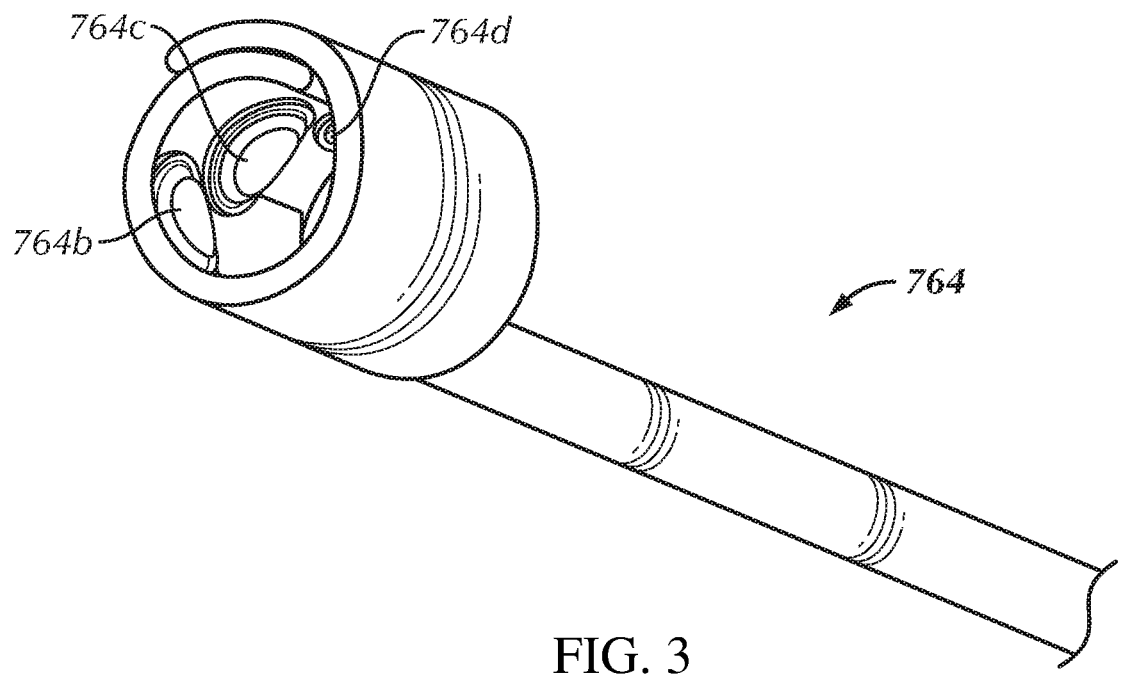
FIG. 3 is a perspective view of the electrode shown in FIG. 1 showing a plurality of contacts.

One exemplary OSA system is illustrated in FIGS. 1-3. In this system, one or more independent current sources drive one or more contacts (e.g., 764*a*, 764*b*, 764*c* and 764*d*) that interface with Hypoglossal nerve (HGN) 322 in order to control the position of tongue 110 of a patient. These contacts may be contained, for example, in a single cuff electrode 764 as shown in FIGS. 2 and 3. In some embodiments, cuff electrode 764 includes a total of six contacts.

In one embodiment, the OSA system is comprised of implanted and external elements which together act to provide continuous open loop targeted selective stimulation of the HGN 322. The implanted elements (i.e. the elements implanted into the patient) may include, for example, an implantable pulse generator (IPG) (not shown) and cuff electrode 764. The external elements may include components such as a remote control and charger (RCC), a charge antenna (CA), and power supply for the patient, and a notebook computer with clinician's software programming system, as described in U.S. Pat. No. 8,428,725, U.S. Patent Application Publication No. US 2011/0112601, and U.S. Pat. No. 8,886,322.

In some embodiments, the IPG may be responsible for generating the pulses that activate the desired neurons within the HGN 322, and is implanted in the anterior chest region of the patient. In further embodiments, cuff electrode 764 may attach to the IPG via an inline connector, and runs from the chest location of the IPG to the sub-mandibular region where it is wrapped around the HGN 322. The IPG preferably contains a plurality of independent current sources (e.g, six, or one for each contact), each capacitively coupled via feedthroughs in its enclosure to the inline connector. The inline connector may have six torroidal spring contacts which may mate with ring contacts of a proximal connector of cuff electrode 764. Each ring contact of the cuff electrode 764 may be connected by a wire in the cuff electrode 764 assembly to a contact within the self-sizing cuff. Each contact may be shaped to match the curvature of the nerve bundle of the HGN 322, and the six contacts are located within the cuff so that six sectors of the nerve circumference are in intimate contact with the cuff contacts. The IPG may be directed by the RCC to start and stop a sleep therapy treatment session, to provide information on the status of the IPG and cuff electrode 764, and is used in conjunction with the CA to replenish the energy within the IPG battery. The software may be used by a clinical engineer or clinician to program the OSA system for use in providing therapy to the patient.

In certain embodiments, each contact of cuff electrode 764 is assigned to one or more functional or muscle groups. Functional groups may in turn be used to select regions of fibers within the nerve bundle that result in a desired tongue movement. The effort of moving the tongue to the desired position is thus shifted from one functional group to another functional group so that no single functional group is required to work all of the time. Thus, the effort of moving the tongue is shared among multiple stimulated nerve fibers and their associated muscles, preventing or reducing fatigue because none of the groups are activated long enough to cause significant fatigue, and during their off, or non-stimulated, state they are allowed to recover from the stimulation. In certain exemplary embodiments, each group is active until just before significant fatigue sets in. One or more additional groups are then activated to take its place, allowing the former muscle group fibers to rest. In one embodiment, the stimulation is spread over more than one contact wherein the duty cycle of each contact is overlapped (see FIG. 4).

Figure 4:
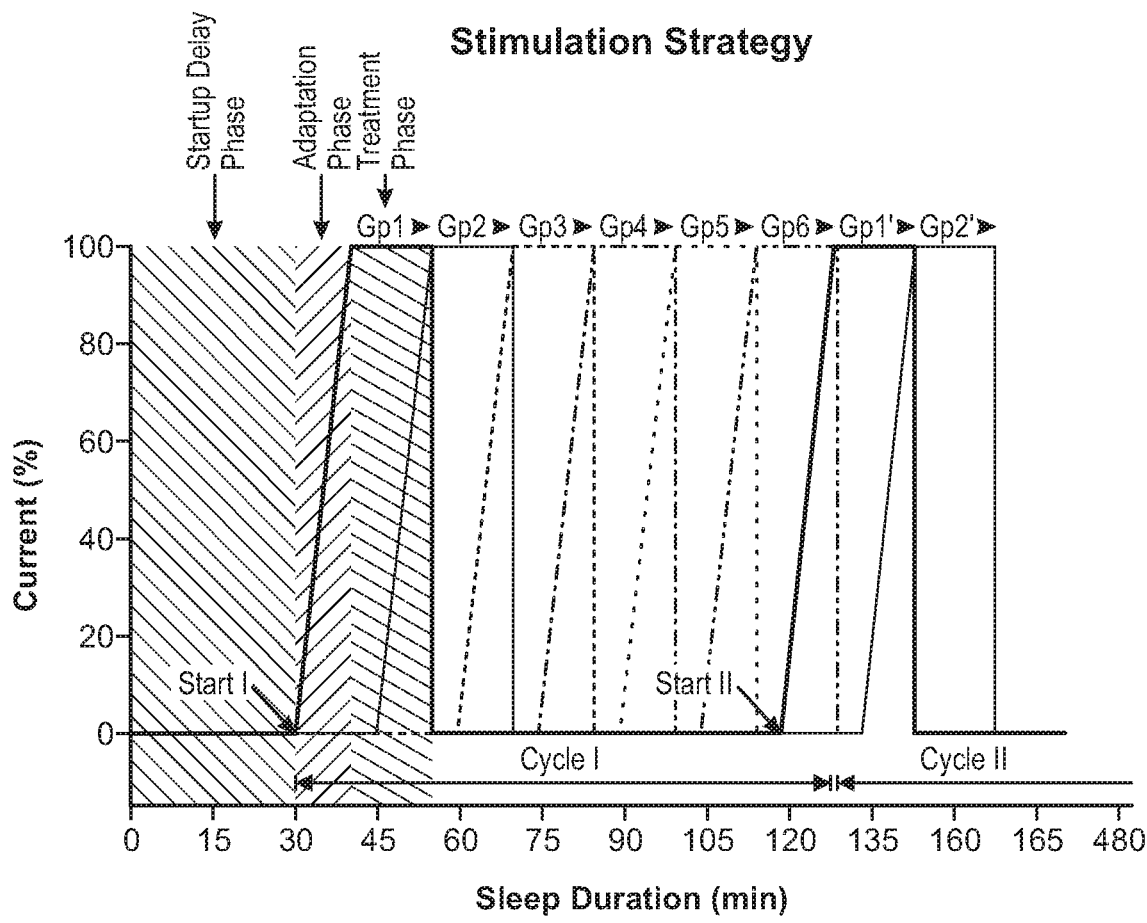
FIG. 4 is a graphical representation of an exemplary stimulation strategy.

As further shown in FIG. 4, functional groups may be used to establish load sharing, amplitude ramping, and delayed start of stimulation to optimize the delivery of stimulation of the targeted nerve (the Hypoglossal nerve, for example). In the exemplary strategy of FIG. 4, stimulation is delayed after a patient begins a sleep session, allowing the patient to fall asleep before stimulation begins. Stimulation from each of the functional groups takes turns ramping up, holding the tongue in the desired position or state for a period of time that is sustainable without significant fatigue, before the next group starts and the previous group stops allowing muscle fibers associated with the previous group to relax, and which helps to prevent fatigue but which maintains desirable tongue position or state all of the time.

Operation of the OSA systems according to some embodiments of the present invention may further include an adjustment or titration phase. In the titration phase, for example, the electrode contacts may be tested to determine their threshold, target and maximum stimulation levels, what the actions of each of the electrode contacts elicits, testing of contact pairs or tripoles, etc., if warranted, and assignment of groups that may be used during patient use.

In some embodiments of the present invention, methods for titrating an OSA system to fit the OSA system to a patient include adjusting one or more stimulation parameters of the OSA system in response to measurements taken from the OSA patient. Such methods may be used, for example, in order to tailor and/or optimize the performance of the OSA system to the specific patient and select the final stimulation parameters for patient use. According to some such embodiments, a method of titrating an OSA system includes adjusting one or more parameters, for example, assignment of contacts to groups, whether or not a contact or group is enabled or disabled, stimulation amplitude, stimulation phase duration, stimulation frequency, group ramp up time, group on time, group ramp down time, group gap time, group population percentages, inter- and intra-therapeutic periodicity, and combinations thereof. Gap time, as used herein, refers to the time that stimulation is not active for that contact or group. Other stimulation parameters of the system as described herein may also be adjusted during titration. The stimulation parameters may be adjusted for one or more of the electrode contacts. In some embodiments, the stimulation parameters are adjusted for each of the electrode contacts, for example, each of the six contacts of cuff electrode 764. In some embodiments, patient comfort during the accommodation phase of treatment, wherein the patient gradually becomes accustomed to the sensation of electrical stimulation, may be assisted by allowing the patient to utilize an additional ramp applicable to all contacts for a desired duration during sleep therapy, and to apply an overall scale reduction in therapeutic levels until the patient is able to fully utilize the therapeutic settings without arousals.

In some embodiments, the one or more stimulation parameters are adjusted to improve one or more physiological measurements obtained from the patient during use of the OSA system. In some embodiments, the one or more stimulation parameters are adjusted to improve at least two physiological measurements obtained from the patient during use of the OSA system. Improvement of a physiological measurement can be determined by a change in the physiological measurement toward a normative value (e.g., a value exhibited by someone that is not suffering from OSA). Such physiological measurements may include, for example, patient's respiratory airflow (e.g., nasal flow and/or oral flow), tidal volume, blood oxygen levels, heart rate, blood pressure, peripheral arterial tone, pulse transit time, electroencephalography, electromyography, electrooculography, sleep state, snoring, and combinations and/or derivatives thereof. Derivatives include values which can be calculated or obtained from the physiological measurements taken of the patient. In some embodiments, derivatives may include, for example, effort, energy cost, $O_2$ consumption, etc. In some embodiments, for example, the physiological measurements may be collected from the patient while the patient is asleep and may be collected automatically or at predetermined times. Preferably the measurements are taken while the patient is in the same sleep position (e.g., supine versus lateral) to minimize variability. Moreover, in some embodiments, the taking of measurements and/or other titration steps are stopped when the patient is in an aroused state or when some other predetermined condition of the patient occurs which could result in an error in the measurements. For example, in some embodiments, an error condition may be realized when one or more of the following occur: positional changes, a predetermined number of changes per hour is exceeded, a predetermined limit on changes is reached, or device/system errors (e.g., loss of telemetry, lack of updated condition stimulation state or PSG signal, etc.). In some embodiments, the method may be stopped or altered if a worsening condition is detected in the one or more physiological measurements.

In certain embodiments, one or more parameters of the OSA system are particularly adjusted to improve airflow through the patient's airway. In some embodiments, the one or more parameters are adjusted in response to measurements of the patient's nasal flow, oral flow, and/or a combination of the nasal and oral flows (total pulmonary airflow) and/or tidal volume. Tidal volume refers to the lung volume representing the normal volume of air displaced between normal inhalation and exhalation when extra effort is not applied. Patient airflow and/or tidal volume can be measured using any suitable technique known in the art. In one embodiment, patient airflow and/or tidal volume is measured using a flow sensor, for example, an additional flow sensor that may be connected to a CPAP mask. In some embodiments, the airflow measurements may be collected and recorded automatically. In some embodiments, tidal volume is not measured directly but is a derivative value that can be obtained from the airflow measurements by integrating the flow signal that is timed to commence from the point at which flow starts during inhalation and stops prior to exhalation. In some embodiments, for example, the one or more parameters (e.g., stimulation amplitude, stimulation phase duration, stimulation frequency, etc.) may be adjusted or increased if the measured air nasal and/or oral flow and/or tidal volume of the patient is less than a desired target value or threshold. In some embodiments, the target value or threshold is a predetermined value. In some embodiments, the target value or threshold is an airflow or tidal volume value for a person that is not suffering from OSA. After the adjustments to the one or more parameters, additional airflow and/or tidal volume measurements can be taken to assess the effect of the adjustments on the patient's airflow and/or tidal volume. If the measured values are still suboptimal relative to the desired target value or threshold, further adjustments to the one or more parameters can be made and the steps repeated until the measured airflow reaches the target value or threshold. For example, incremental adjustments in the values of one or more stimulation parameters can be made, with airflow measurements taken after each adjustment, until the target value or threshold has been met.

In some embodiments, the one more parameters of the OSA system are adjusted to improve a patient's oxygen saturation level, for example, peripheral capillary oxygen saturation ($SpO_2$). The oxygen saturation level (e.g., $SpO_2$) can be measured using any suitable technique known in the art. For example, in some embodiments, oxygen saturation level measurements may be made using a finger pulse oximeter. In some embodiments, the oxygen saturation level measurements may be collected and recorded automatically. In certain embodiments, the one or more parameters (e.g., stimulation amplitude, stimulation phase duration, stimulation frequency, etc.) may be adjusted or increased if the measured oxygen saturation level is less than a desired target value or threshold. In some embodiments, the target value or threshold is a predetermined value. In some embodiments, the target value or threshold is an oxygen saturation level for a person that is not suffering from OSA. After the adjustments to the one or more parameters, additional measurements can be taken to assess the effect of the adjustments on the patient's oxygen saturation level. If the measured values are still suboptimal relative to the desired target value or threshold, further adjustments to the one or more parameters can be made and the steps repeated until the measured oxygen saturation level reaches the target value or threshold. For example, incremental adjustments in the values of one or more stimulation parameters can be made, with oxygen saturation levels taken after each adjustment, until the target value or threshold has been met.

In some embodiments, titration of the OSA system based on a patient's oxygen saturation level may be used as an alternative to titration based on patient airflow. In other embodiments, both patient airflow (e.g., nasal flow and/or oral flow) and oxygen saturation level (e.g., $SpO_2$) are measured. In some such embodiments, both the airflow and oxygen saturation levels must improve before a change to the one or more stimulation parameters is accepted for patient use. For example, if an increase in a stimulation parameter (e.g., stimulation amplitude or frequency) for a particular contact results in increased airflow but not increased oxygen saturation level, the increase in the stimulation parameter for the contact may not be used.

The one or more stimulation parameters can also be adjusted in response to other measurements obtained from the patient according to certain embodiments. In some embodiments, for example, the patient's sleep state can also be measured (e.g., via electroencephalography) and used to determine adjustments to the one or more stimulation parameters in addition to or as an alternative to airflow and/or oxygen saturation level. In some embodiments, an improvement in a patient's sleep state can be measured, for example, as a decrease in the number of arousals or microarousals. In some embodiments, change in a patient's sleep state can be determined, for example, via monitoring changes in eye movement, leg movement, electroencephalography, electromyography, electrooculography, REM sleep, or combinations thereof.

The one or more stimulation parameters can also be adjusted in response to other measurements obtained from the patient according to certain embodiments. In some embodiments, for example, the patient's blood pressure or arterial tone can also be measured (e.g., via pulse transit time (PTT) or peripheral artery tone (PAT)) and used to determine adjustments to the one or more stimulation parameters in addition to or as an alternative to airflow and/or oxygen saturation level. In some embodiments, an improvement in a patient's sleep state can be measured, for example, as a decrease in PTT or PAT.

In one embodiment, a method of titrating an OSA system includes stimulating one electrode contact or group at a time, comparing physiological measurements (e.g., airflow and/or oxygen saturation level) taken during stimulation and when stimulation is off, using stimulation on time to control how long stimulation is applied, and using gap time to control how long stimulation is off, adjusting one or more stimulation parameters, and verifying that the adjustments to the one or more stimulation parameters leads to improved physiological measurements when the stimulation is provided compared to when stimulation is off. For example, in some embodiments, stimulation is turned on for two breaths and turned off for the next two breaths, with the physiological measurements taken during each set. In other embodiments, stimulation is turned on for one breath and turned off for one breath. In yet other embodiments, stimulation is turned on for more than two breaths and turned off for more than two breaths. In further embodiments, a method of titrating an OSA system includes stimulating the electrode contacts or groups during therapy, keeping a running average of the physiological measurements (e.g., airflow and/or oxygen saturation level), and adjusting the stimulation parameters to improve the physiological measurements. These steps may be repeated with incremental adjustments being made to the stimulation parameters each time until, for example, the desired improvement is achieved, the stimulation parameter reaches a pre-set limit, or it is otherwise determined that adjustment of that particular stimulation parameter does not lead to an improvement. The steps may also be repeated for each of the electrode contacts or groups. In some embodiments, a method further includes comparing the performance of each electrode contact or group and using a threshold to determine which contact(s) or group(s) to use during therapy. Example data that may be collected during the parameter adjustments include maximum airflow, minimum airflow, average airflow, maximum oxygen saturation level, minimum oxygen saturation level, and/or average oxygen saturation level. These data may be collected for each of the electrode contacts or groups.

As described, it may be desirable to adjust stimulation parameters when more than one group or contact is enabled. After initial titration is performed on each group or contact individually, and groups and or contacts are determined and enabled that provide useful function for the therapy the patient performance may be monitored during normal cyclical use of the system. Because the IPG and lead are implanted, there may not be a direct method available to know which group/contact is active, but it may be desirable to adjust group/contacts as observations confirm that stimulation parameter changes are required. In polysomnography (PSG) operation the IPG may wirelessly send or broadcast information to the RCC when it changes from one group/contact to another. The RCC, upon receiving this information may make this information available to the clinician through the system software, and may also generate two signals that are recorded by the PSG system. One signal may indicate which group/contact is active by generating a number of pulses corresponding to the number of the group or contact. For example, if group three becomes active the IPG sends a message to the RCC, the RCC receives this message and it generates three pulses on this line to the PSG system. In some embodiments, the amplitude of the contact may also be broadcast by the IPG. This information may be encoded by the RCC on a second line that is attached to the PSG system. The encoded amplitude information may include a series of pulses that indicate the range of the amplitude, followed by a constant level signal that indicates the level of the signal within this amplitude range. The amplitude information that is sent to the PSG system may be most useful in post-analysis of the PSG data, as the IPG amplitude is already known to the clinical software system, but which group becomes active is only known to the IPG. In this way the clinician may be alerted to which contact is active and therefore which may be in need of adjustment, and the adjustment may be made while the therapy is active. The incorporation of the group and amplitude signals into the PSG record may also allow post analysis of the performance of the implanted system with respect to breathing performance indices.

As described, adjustments to the one or more stimulation parameters during the titration may be made in incremental changes according to some embodiments. For example, the stimulation parameters may be increased or decreased in increments based upon any percentage of the existing levels, for example ±5 or ±10%, or by incremental changes, for instance, 5, 10, 25 or 50 µA step sizes for amplitude adjustments. In some embodiments, the stimulation parameters are increased or decreased by a predetermined percentage or predetermined step amount. These example values should not be considered limiting, and those skilled in the art will understand that other methods or levels of stimulation adjustment are possible. In some embodiments, the stimulation parameters are adjusted within pre-set limits. In further embodiments, the stimulation parameters are adjusted with a limited rate of change. In some embodiments, stimulation levels previously determined to cause discomfort or arousal may be used as limits for the stimulation adjustments. In some embodiments, stimulation levels below which insufficient therapeutic effects are produced may also be used as limits for the stimulation adjustments.

In some embodiments, the titration methods described herein may allow a clinical engineer or clinician to fit the OSA system onto a patient and determine the optimal stimulation parameters (e.g., stimulation amplitude and/or frequency) for each of the electrode contacts. In some embodiments, the parameter values obtained through the titration methods may be inputted, for example, into a Titration Screen of the software used by the clinical engineer or clinician to program the OSA system, which may include controls for the stimulation parameters (e.g., amplitude, frequency, etc.) where threshold, target and maximum stimulation parameters are determined for each of the six contacts of the system. In some embodiments, the titration methods described herein may allow the clinical software to automatically adjust levels of stimulation based upon measured and analyzed physiological signals under the guidance of the clinical engineer or clinician.

The embodiments described herein may include or utilize one or more computers having one or more processors and memory (e.g., one or more nonvolatile storage devices). In some embodiments, memory or computer readable storage medium of memory stores programs, modules and data structures, or a subset thereof for a processor to control and run the various systems and methods disclosed herein. In one embodiment, a non-transitory computer readable storage medium having stored thereon computer-executable instructions which, when executed by a processor, perform one or more of the methods disclosed herein.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

We claim:

1. A method for providing stimulation comprising at least one stimulation parameter via one or more electrode contacts in a system for stimulating a hypoglossal nerve of a patient, the method comprising:
   activating one of the one or more electrode contacts to stimulate the hypoglossal nerve of the patient;
   obtaining a first physiological measurement from the patient;
   comparing the first physiological measurement to a first predetermined target value;
   adjusting a stimulation parameter for the one of the one or more electrode contacts in response to the first physiological measurement differing from the first predetermined target value, constituting an adjustment step;
   performing one or more additional adjustment steps until the physiological measurement reaches the first predetermined target value or the stimulation parameter reaches a pre-set limit; and
   programming an implantable pulse generator of the system for stimulating the hypoglossal nerve of the patient to deliver open loop targeted selective stimulation to the hypoglossal nerve of the patient after the physiological measurement reaches the first predetermined target value or the stimulation parameter reaches the pre-set limit.

2. The method of claim 1, wherein the stimulation parameter is changed incrementally during the adjustment step.

3. The method of claim 2, wherein stimulation parameter is changed by a percentage of an existing value of the stimulation parameter during the adjustment step.

4. The method of claim 1 further comprising:
wirelessly transmitting information to a display and/or recording device regarding which of the one or more electrode contacts is activated.

5. The method of claim 4, wherein the information includes an identity of an activated electrode contact, and the method further comprising:
generating a number of pulses corresponding to the identity of the activated electrode contact.

6. The method of claim 5, wherein the information includes an amplitude of the activated electrode contact, and the method further comprising:
generating a number of pulses corresponding to an amplitude scale of the amplitude and generating a voltage level corresponding to the amplitude within the amplitude scale.

7. The method of claim 1 further comprising:
obtaining a second physiological measurement from the patient, comparing the second physiological measurement to a second predetermined target value, and adjusting a stimulation parameter for the one of the one or more electrode contacts in response to the second physiological measurement differing from the second predetermined target value.

8. The method of claim 7, wherein the first and second physiological measurements are selected from the group consisting of nasal airflow, oral airflow, tidal volume, blood oxygen saturation level, blood pressure, peripheral arterial tone, pulse transit time, electroencephalography, electromyography, electrooculography, and combinations and/or derivatives thereof.

9. The method of claim 1, wherein the method is performed while the patient is asleep.

10. The method of claim 9, wherein adjustment of the stimulation parameter is paused while an arousal of the patient is detected, a worsening or altered condition of the first physiological measurement is detected, or a predetermined condition of the patient is detected.

11. The method of claim 1, wherein the system is configured for preventing obstructive sleep apnea in the patient.

12. The method of claim 11, wherein the first predetermined target value is a value of a person who does not have obstructive sleep apnea.

13. The method of claim 1, wherein the stimulation parameter is selected from the group consisting of stimulation amplitude, stimulation phase duration, stimulation frequency, contact group assignment, group or contact enablement, group ramp up time, group on time, group ramp down time, group gap time, group population percentage, inter- and intra-therapeutic periodicity, and combinations thereof.

14. The method of claim 1, wherein the first physiological measurement is selected from the group consisting of nasal airflow, oral airflow, tidal volume, blood oxygen saturation level, blood pressure, peripheral arterial tone, pulse transit time, electroencephalography, electromyography, electrooculography, and combinations and/or derivatives thereof.

15. The method of claim 1 further comprising:
repeating the method for each of the one or more electrode contacts or each of one or more electrode groups in the system.

16. The method of claim 1, wherein the one or more electrode contacts includes a plurality of electrode contacts, each electrode contact being connected to an independent current source.

17. The method of claim 1, wherein the system for stimulating a hypoglossal nerve of a patient includes six electrode contacts arranged on a cuff electrode and is configured for controlling a position of the patient's tongue.

18. The method of claim 1 further comprising:
obtaining a second physiological measurement from the patient;
comparing the second physiological measurement to a second predetermined target value;
performing an adjustment step in response to the second physiological measurement differing from the second predetermined target value; and
performing one or more adjustment steps until the first physiological measurement reaches the first predetermined target value and/or the second physiological measurement reaches the second predetermined target value, or until the stimulation parameter reaches the pre-set limit.

19. The method of claim 18, wherein the first and second physiological measurements are selected from the group consisting of nasal airflow, oral airflow, tidal volume, blood oxygen saturation level, blood pressure, peripheral arterial tone, pulse transit time, electroencephalography, electromyography, electrooculography, and combinations and/or derivatives thereof.

20. The method of claim 19, wherein the stimulation parameter is selected form the group consisting of stimulation amplitude, stimulation phase duration, stimulation frequency, contact group assignment, group or contact enablement, group ramp up time, group on time, group ramp down time, group gap time, group population percentage, inter- and intra-therapeutic periodicity, and combinations thereof.

21. The method of claim 18 further comprising:
repeating the method for each of the one or more electrode contacts or each of one or more electrode groups in the system.

22. The method of claim 18, wherein the system for stimulating a hypoglossal nerve of a patient includes six electrode contacts arranged on a cuff electrode and is configured for controlling a position of the patient's tongue.

23. The method of claim 1, wherein the method is managed under algorithmic control by a clinical software system under the supervision of a clinician or engineer.

* * * * *